Figure 1:
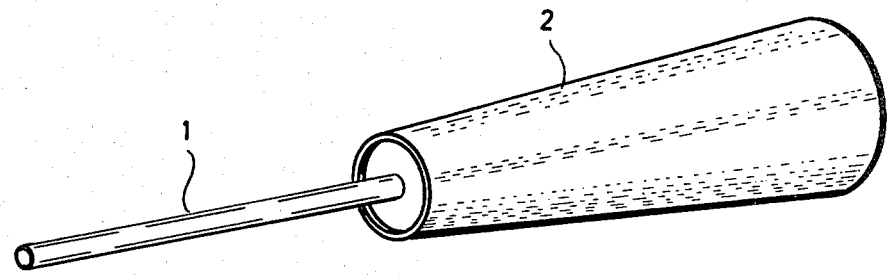

United States Patent [19]

Kumbrant

[11] 4,206,652
[45] Jun. 10, 1980

[54] SAMPLER

[76] Inventor: Lars A. T. Kumbrant, Box 23, S-190 63 Örsundsbro, Sweden

[21] Appl. No.: 7,205

[22] Filed: Jan. 29, 1979

[30] Foreign Application Priority Data

Jan. 30, 1978 [SE] Sweden .................. 7801111

[51] Int. Cl.² ............................................ G01N 1/12
[52] U.S. Cl. ............................................ 73/425.4 R
[58] Field of Search ......... 73/421 R, 425.4 R, DIG. 9

[56] References Cited

U.S. PATENT DOCUMENTS

| 3,791,219 | 2/1974 | Falk | 73/DIG. 9 |
| 3,897,689 | 8/1975 | Boron | 73/425.4 R |
| 3,994,172 | 11/1976 | Kelsey | 73/425.4 R |

FOREIGN PATENT DOCUMENTS 2457098 6/1975 Fed. Rep. of Germany ...... 73/DIG. 9

Primary Examiner—S. Clement Swisher
Attorney, Agent, or Firm—Witherspoon & Hargest

[57] ABSTRACT

Sampler for drawing samples from melt comprising an inlet tube (1) and a sample container (3) and a sleeve (2) at least surrounding the sample container (3). The novelty features of the invention reside in the fact that the sleeve (2) has the shape of a truncated cone and in that the sample container (8) is located in the tapered sleeve (2) at its end with a smaller diameter.

3 Claims, 3 Drawing Figures

U.S. Patent Jun. 10, 1980 4,206,652

SAMPLER

The present invention relates to samplers and more precisely to a sampler for drawing samples from molten metal.

There exist indeed many known samplers for drawing samples from melt which are intended to be used under different operating conditions and for drawing different kinds of samples. In that connection it has been desired to have a sampler with a relatively long sampling tube, which can be used for sucking the sample into the sample container by means of vacuum.

Many attempts have been made to produce such a sampler but they have generally suffered from certain deficiencies. Since the best material for the tube into the sample container is quartz glass it has been desirable to use tubes of quartz glass. However, this has resulted in that many samplers have had their glass tube smashed during transport and during storing since it has not been possible to protect this in a simple and economic way and accordingly it has usually been left unprotected. It has also been difficult to produce a proper and simple sealing between the handle, the so-called lance, and the sampler and for this reason air has often leaked in at that spot and this has caused the sampler to malfuntion.

Attempts have indeed been made to embed the sample container itself in a cylindrical tube section from one end of which the glass tube projects and the other end of which is intended to be threaded unto the holder part of the lance. In connection with such design it has, in order to make a sleeve, which projects out over the glass tube as a cover for this, and which sticks to the cylindrical tube section been necessary to use a special kind of attachment as for instance adhearing or gluing. It has thereby been experienced that the glass tube has been broken off when attempts have been made to remove the protective sleeve. It is furthermore a relatively expensive operation to carry out such a fastening to an article of the kind in question, since it is a production goods which is produced in millions. The fastening is, however, necessary since the tube section and the cover cannot, to reasonable costs, be manufactured with such precision that a force fit is provided.

A structure of the kind mentioned above has furthermore another disadvantage since it is difficult to remove the sample container with the drawn sample from the tube section. If the tube section is made of paper material, which is very common, the sample container must be removed rapidly from this since in other case the tube section may catch fire due to the heat from the sample, and this renders the removal more difficult.

The object of the present invention is to eliminate the above mentioned disadvantages. This object is attained with a sampler of the kind indicated in the claims, from which also the specific characteristics of the invention are clear.

Figure 2:
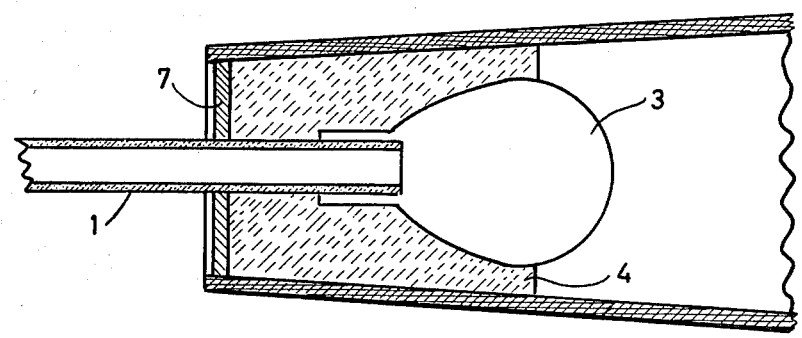
Figure 3:
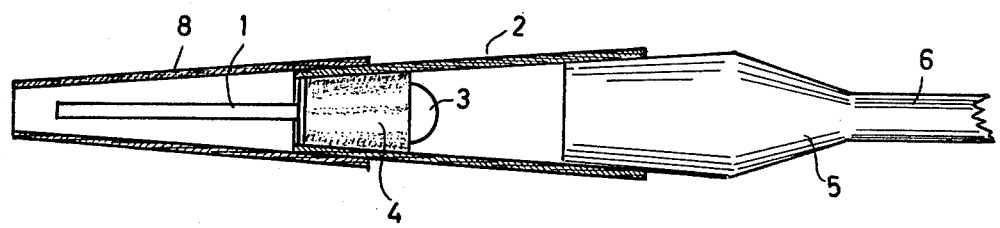

The invention is more closely described below in connection with the enclosed drawings, in which FIG. 1 is a perspective view of a sampler according to the invention with the protective sleeve removed, FIG. 2 is a fragmentary section through the sampler in FIG. 1 showing the sampler and the mounting of the glass tube in this, and FIG. 3 is a schematic, fragmentary view partly in section showing a sampler according to the invention seated on a sampling lance and with a cover over the glass tube.

The sampler shown in FIG. 1 consists of a quartz-glass tube 1 and a tapered sleeve 2, in which the sample container 3 is contained, at least partly embedded in a sand body 4. The sand body 4 and the sample container 3 may have different shapes and do not constitute any part of the proper invention. The glass tube 1 projects from the smaller end of the tapered sleeve 2 substantially in the centre thereof and the axis of the tube 1 coincides with the longitudinal axis of the tapered sleeve 2.

The larger end of the tapered sleeve 2 is open and is intended for receiving the holder part 5 of a sampling lance 6. When a negative pressure is created in the tapered sleeve 2 through the lance 6 it is important that leakage does not occur anywhere but that the sample of the melt is sucked up through the tube 1 as rapidly as possible. Besides at the attachment of the holder part 5 to the tapered sleeve 2 leakage may occur through the sand body 4 in the area around the glass tube 1. As a protection against this in the area around the glass tube 1 the sand body 4 may in that area be covered with a layer of cement or other sealing, heat resistant material. Alternatively an annular disk made of cardboard or other suitable material may, as is shown in FIG. 2, be squeezed into the tapered sleeve 2. This annular disk 7 does then provide the necessary sealing which may be reinforced by the application of some kind of suitable glue or other suitable sealing means around the tube 1 where this extends through the disk 7.

Such a glue or sealing means contributes to the retaining of the sand body 4 and the sample container 3 with the glass tube 1 in place in the tapered sleeve 2. Furthermore the tapered sleeve has the advantage, with respect to especially this attachment, that it is sufficiently strong to retain said elements during normal handling of the sampler, while on the other hand, when these elements after the sampling are to be removed, this may be carried out very easily simply by pounding the base of the tapered sleeve against a hard surface, as it has been experienced that the sleeve then very easily released from the sand body and due to the tapered shape of the sleeve as well as the sand body it is obvious that when the sand body has once get loose from the sleeve there is no friction holding it in place.

The fact that this removal may be done very quickly and easily is very substantial since this sleeve, which is usually made of an inflammable material, easily catches fire due to the heat from the sample if it is not removed quickly. If the sleeve of the sampler catches fire it is clear that the sampler cannot be handled until the fire is out or is put out. Extinguishing of the fire which involves rapid cooling may however affect the sample in an undesirable way and should be avoided. By previously known samplers with cylindrical sleeves such fire has been relatively common due to the fact that it has not been possible to remove the sand body with the sample container through the sleeve in a simple way due to internal friction and it has in such cases usually been necessary to crash the sand body with a blow from some hard object in order to remove the sample container.

It may seem simple to exchange a cylindrical sleeve for a tapered sleeve. However, regarding the advantages obtained hereby they are unexpectedly great and if such a procedure had been obvious the sampler according to this invention would have been in the market many years ago. It has probably been considered that the sand body has not been satisfactory fastened in the sleeve in such a structure with a tapered sleeve. However, it has been experienced that in this respect two advantages are obtained namely, a satisfactory retaining for normal use of the sampler and a simple removal of the sampler from the tapered sleeve.

The tapered shape of the sleeve 2 does, however, also provide the following advantages: The holder part 5 of the lance 6 will be rigidly attached to the inner-wall of the sleeve with a large surface contact, which also provides for a good sealing without special measures. A protective sleeve 8 can easily be placed over the glass tube 1 and is by a press-fit favourably secured to the outer side of the tapered sleeve 2 without any further fasteners, also by inadequate tolerances on the different parts.

In certain embodiments of the invention there is no need for a sand body 4, for instance if the sample container 3 forms an extension of the inlet tube 1. In such a case it is quite sufficient if the inlet tube 1 is glued to the disk 7. However, there may be provided a guiding material around the sample container 3 in the tapered sleeve 2 in order to assist in holding this in place during transport and storing. It may however occur that a small amount of the sample material leaks out through some joint in the sample container or where the air is evacuated from the sample container, and this material reaches the inner-wall of the tapered sleeve. However, due to the tapered shape of the sleeve, such material cannot cause friction against the inner-walls of the sleeve during the removal of the sample container and this removal is thus carried out rapidly and easily, while on the other hand in a cylindrical sleeve such material could cause friction against the inner-wall and could thus render the removal of the sample container more difficult.

With the present invention a substantial improvement has been made in the field in question as regards the practical handling of the sample as well as the simple and inexpensive manufacturing thereof.

What I claim is:

1. Sampler for drawing samples from melt comprising a sleeve in the form of a truncated cone, an inlet tube extending into the end of said sleeve having the smaller diameter, said tube extending substantially along the longitudinal axis of said sleeve, the end of said sleeve having the larger diameter being open to receive the holder part of a sampling lance the surface of which is tapered to mate with a corresponding tapered surface of said sleeve to sealingly attach said sleeve to said holder part, and a sample container placed in said sleeve at its end having the smaller diameter, said inlet tube extending into said sample container.

2. Sampler according to claim 1 including an annular disk positioned internal of said sleeve at the end thereof having the smaller diameter, the edge of said disk sealingly engaging the internal surface of said sleeve, said disk including an aperture substantially in the center thereof through which said tube extends.

3. Sampler for drawing samples from melt, which comprises an inlet tube, a sample container and a sleeve which surrounds at least the sample container, said sleeve being shaped as a truncated cone, said sample container being placed in the tapered sleeve at its end having the smaller diameter, and a removable protective sleeve in the shape of a truncated cone, with substantially the same cone angle as the tapered sleeve, being placed over the inlet tube and fastened to the tapered sleeve surrounding the sample container by a press-fit.

* * * * *